(12) United States Patent
Pursley

(10) Patent No.: US 10,092,386 B1
(45) Date of Patent: Oct. 9, 2018

(54) MULTI LUMEN IVC FILTER RETRIEVAL DEVICE

(71) Applicant: Matt D. Pursley, Dawsonville, GA (US)

(72) Inventor: Matt D. Pursley, Dawsonville, GA (US)

( * ) Notice: Subject to any disclaimer, the term of this patent is extended or adjusted under 35 U.S.C. 154(b) by 103 days.

(21) Appl. No.: 15/091,411

(22) Filed: Apr. 5, 2016

Related U.S. Application Data

(63) Continuation-in-part of application No. 14/214,273, filed on Mar. 14, 2014, now Pat. No. 9,592,079, and a continuation-in-part of application No. 14/214,344, filed on Mar. 14, 2014, now Pat. No. 9,301,828.

(60) Provisional application No. 61/780,982, filed on Mar. 14, 2013, provisional application No. 61/781,007, filed on Mar. 14, 2013.

(51) Int. Cl.
*A61F 2/01* (2006.01)

(52) U.S. Cl.
CPC ......... *A61F 2/013* (2013.01); *A61F 2002/011* (2013.01)

(58) Field of Classification Search
CPC ............ A61M 25/04; A61M 2025/018; A61M 25/1002; A61M 2025/0177; A61M 25/09041; A61M 25/01; A61F 2/013; A61F 2002/011; A61F 2/01; A61B 2017/320733; A61B 17/32056; A61B 2017/320716; A61B 17/221; A61B 2017/2217; A61B 17/3205; A61B 17/32053
See application file for complete search history.

(56) References Cited

U.S. PATENT DOCUMENTS

| 7,651,503 | B1* | 1/2010 | Coe | A61B 17/320016 |
| | | | | 606/108 |
| 9,592,079 | B1* | 3/2017 | Pursley | A61B 17/50 |
| 2003/0032936 | A1* | 2/2003 | Lederman | A61B 18/1492 |
| | | | | 604/507 |
| 2003/0065335 | A1* | 4/2003 | Guido | A61B 17/12013 |
| | | | | 606/144 |
| 2004/0138685 | A1* | 7/2004 | Clague | A61B 17/12 |
| | | | | 606/167 |
| 2005/0154344 | A1* | 7/2005 | Chang | A61B 17/12136 |
| | | | | 604/6.09 |
| 2005/0154378 | A1* | 7/2005 | Teague | A61B 17/221 |
| | | | | 606/2.5 |

(Continued)

*Primary Examiner* — Katrina Stransky
(74) *Attorney, Agent, or Firm* — Jeffrey L. Thompson; Thompson & Thompson, P.A.

(57) ABSTRACT

A device for retrieving items endovascularly includes a sheath having a first lumen containing a snare that can be deployed out a distal end of the sheath and retracted back into the sheath for pulling an IVC filter into the sheath. The sheath has a second lumen that opens through a sidewall of the sheath proximal of the distal end. The second lumen contains a removal assist device that can be deployed through the sidewall and used to dislodge and/or cut an item to be retrieved from a vein wall. The removal assist device includes a catheter, a cutting head, and a pull wire. The pull wire has a proximal portion protruding from a proximal end of the catheter and a distal end connected to the cutting head. The pull wire is movable within the catheter to selectively extend and retract the cutting head from the distal end of the catheter.

18 Claims, 16 Drawing Sheets

(56) References Cited

U.S. PATENT DOCUMENTS

| | | | |
|---|---|---|---|
| 2007/0038022 A1* | 2/2007 | Nakao | A61B 17/0469 600/104 |
| 2011/0118769 A1* | 5/2011 | Bliss | A61B 17/320016 606/159 |
| 2014/0180267 A1* | 6/2014 | Vetter | A61B 10/0266 606/33 |

* cited by examiner

MULTI LUMEN IVC FILTER RETRIEVAL DEVICE

RELATED APPLICATIONS

This application is a continuation-in-part of Applicant's copending U.S. patent application Ser. No. 14/214,344 filed on Mar. 14, 2014, and a continuation-in-part of Applicant's copending U.S. patent application Ser. No. 14/214,273 filed on Mar. 14, 2014. This application also claims the benefit of U.S. Provisional Patent Application Nos. 61/781,007 and 61/780,982, both of which were filed on Mar. 14, 2013. The entire contents of the priority applications are incorporated herein by reference.

BACKGROUND OF THE INVENTION

Field of the Invention

The present invention relates generally to catheters, and in particular to catheters that can be used to assist in removal of items endovascularly.

Description of the Related Art

Inferior vena cava filters ("IVC filters") are medical devices that can be implanted into the inferior vena cava to prevent pulmonary emboli (PE). IVC filters are sometimes recommended for patients with contraindications to anticoagulation who either have acute PE or acute proximal (above the knee) deep vein thrombosis. IVC filters are normally placed by compressing them into a thin catheter, and inserting them via a blood vessel, such as the femoral vein, the internal jugular vein, or the arm veins. Once the distal end of the catheter reaches the IVC, the IVC filter is pushed through the catheter and deployed into the desired location.

IVC filters are typically attached to the vena cava by hooks on their ends. Some IVC filters are compression springs, which compress outward onto the sidewall of the vena cava; however, they still have small hooks that retain their location. These hooks aid in the anchoring and healing process, but they make it difficult to retrieve the IVC filter from the vena cava.

FIG. 1 shows an IVC filter 1 deployed in the inferior vena cava. IVC filters 1 are generally anchored by anchors 4 to prevent them from migrating. IVC filters 1 are removed by using a snare 2 and a retrieval sheath 3. Coupling the snare with the IVC filter 1 is difficult. The IVC filter 1 may not be vertically aligned making it difficult to snare. Body movement due to respiration and blood flow also make snaring the IVC filter 1 difficult.

As can be seen in FIG. 1, the snare 2 is attached to the top of the filter 1. As shown in FIG. 2, the sheath 3 is pushed down over the filter 1, capturing the filter 1 and its contents and removing the filter anchors 4 from the vein wall. This allows the filter 1 to be removed. However, on occasion the filter anchors 4 or a portion of the filter 1 become embedded to the vein wall, and this removal procedure cannot be performed.

There is a need for an improved tool to assist with the removal of IVC filters.

SUMMARY OF THE INVENTION

An object of the present invention is to provide a device and method for assisting with the removal of IVC filters.

To accomplish these and other objects of the present invention, a device for retrieving items endovascularly includes a sheath having a first lumen containing a snare that can be deployed out a distal end of the sheath and retracted back into the sheath for pulling an IVC filter into the sheath. The sheath has a second lumen that opens through a sidewall of the sheath proximal of the distal end. The second lumen contains an additional device, such as a balloon, imaging device, diagnostic catheter for infusing contrast media, or a removal assist device. The removal assist device can be deployed through the sidewall and used to dislodge and/or cut an item to be retrieved from a vein wall. The removal assist device includes a catheter, a cutting head, and a pull wire. The pull wire has a proximal portion protruding from a proximal end of the catheter and a distal end connected to the cutting head. The pull wire is movable within the catheter to selectively extend and retract the cutting head from the distal end of the catheter.

According to one aspect of the present invention, a device for retrieving items endovascularly is provided, comprising: a sheath having a first lumen containing a snare that can be deployed out a distal end of the sheath and retracted back into the sheath; the sheath having a second lumen that opens through a sidewall of the sheath proximal of the distal end.

Numerous other objects of the present invention will be apparent to those skilled in this art from the following description wherein there is shown and described an embodiment of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings:

FIG. 9 is an elevation view of the removal assist device;

FIG. 10 is a partial cutaway view of the removal assist device;

FIG. 11 is a perspective view of the removal assist device; and

FIG. 12 is a partial cutaway view of the removal assist device.

FIG. 13 is an elevation view of the tubular cutting head;

FIG. 14 is a perspective view of the tubular cutting head;

FIG. 15 is another perspective view of the tubular cutting head; and

FIG. 16 is another perspective view of the tubular cutting head.

DETAILED DESCRIPTION OF THE INVENTION

A multi lumen IVC filter retrieval device according to the present invention will be described in detail with reference to FIGS. 3 to 16 of the accompanying drawings.

Figure 1:
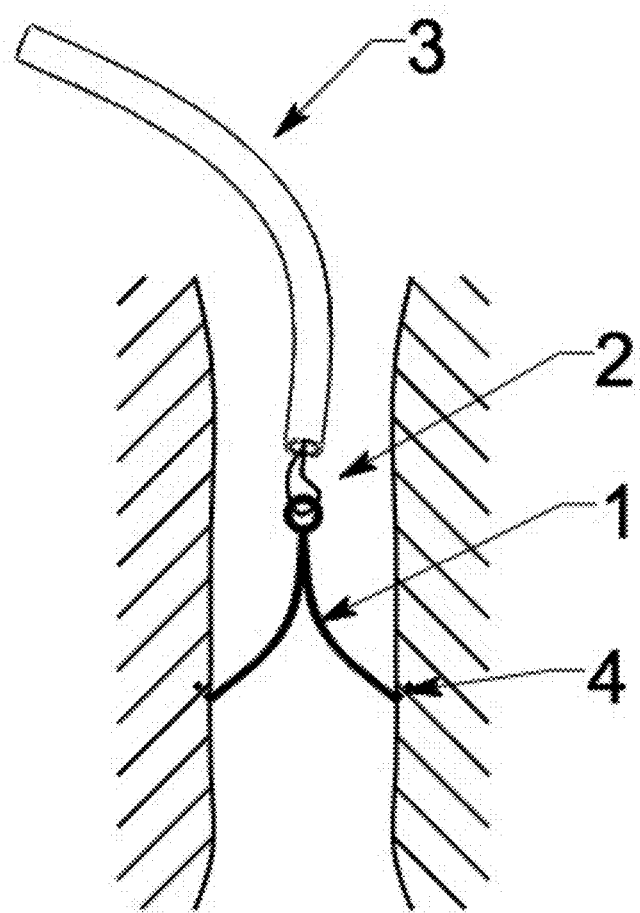
FIG. 1 is illustrates a conventional retrieval sheath for removing an IVC filter deployed in the inferior vena cava.
Figure 2:
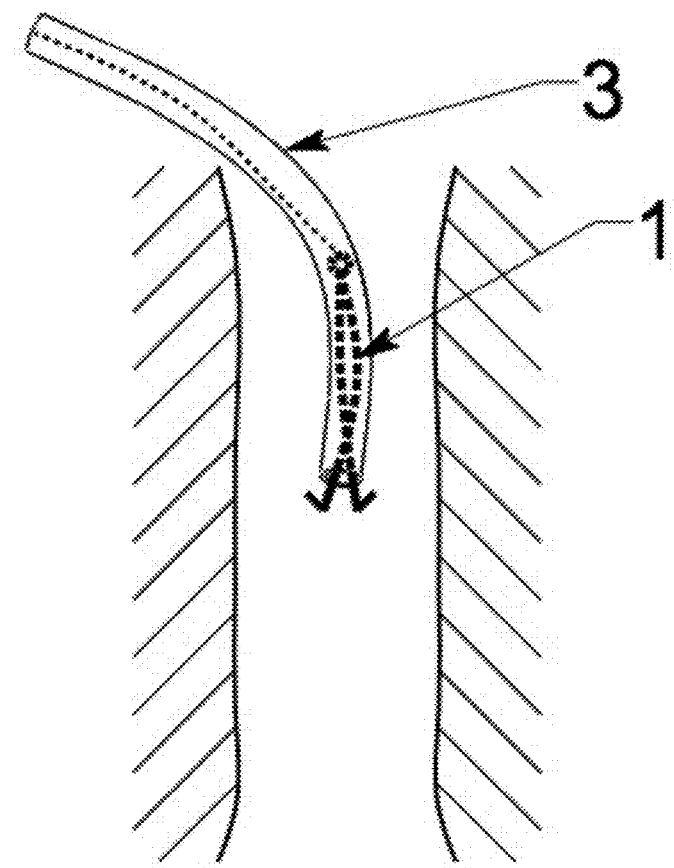
FIG. 2 illustrates the process of using the conventional retrieval sheath shown in FIG. 1.
Figure 3:
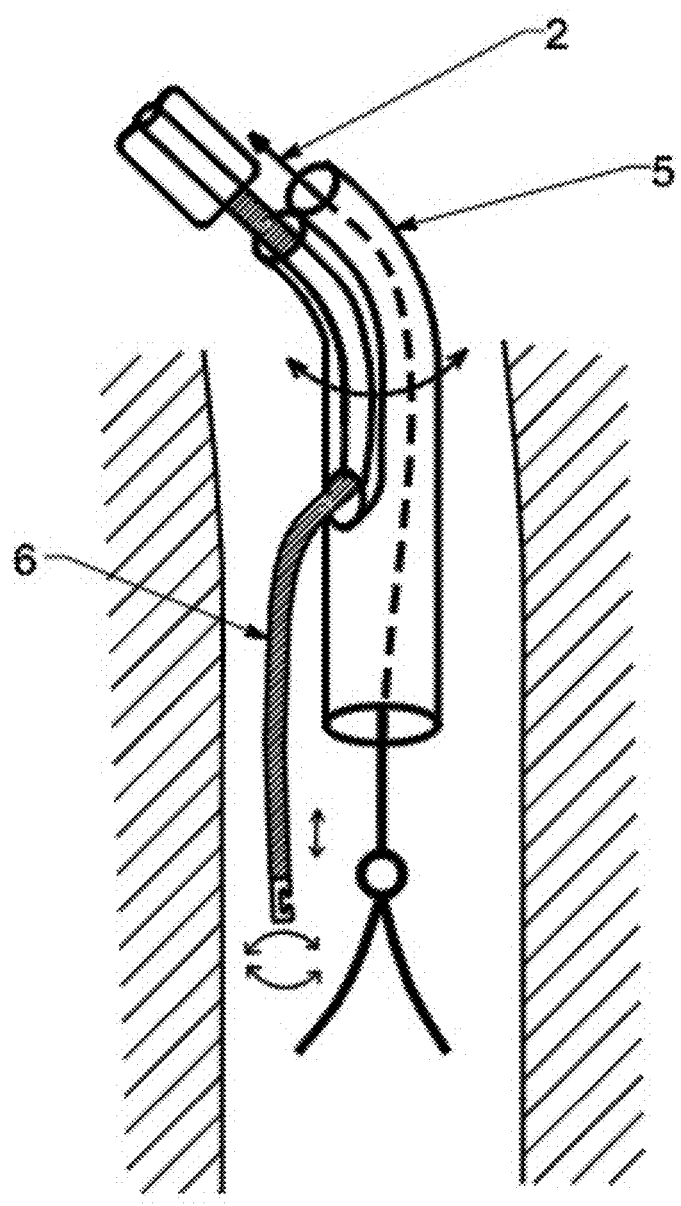
FIG. 3 is an elevation view of a multi lumen IVC filter retrieval device of the present invention as it is being deployed to a location above an IVC filter to be removed.
Figure 4:
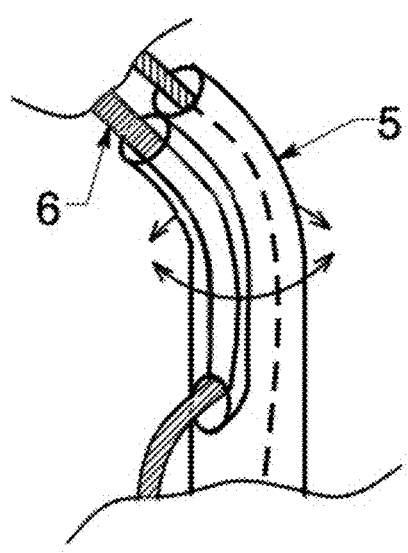
FIG. 4 is a perspective view of the multi lumen IVC filter retrieval device of the present invention.

The multi lumen IVC filter retrieval device is shown in FIGS. 3 and 4. As can be seen, the device uses the same snare and sheath concept as in the conventional filter retrieval device illustrated in FIGS. 1 and 2, except that it also adds a second lumen in the proximal portion of the sheath through which additional devices can be passed, such as balloons, imaging devices, diagnostic catheters for infusing contrast media, laser cutters, or a removal assist device 6, if necessary.

The removal assist device 6 includes a catheter 7, a cutting head 8, and a pull wire 9 to actuate and/or retract the cutting head 8. The cutting head 8 can also be referred to as a holding/cutting head because it serves a dual function of holding and cutting the items to be removed. The cutting head 8 has a generally C-shaped structure with an open lateral side 8a for receiving a portion of an item 10 to be held or cut. The C-shaped structure has a distal portion and a proximal portion with the open lateral side 8a located between the distal portion and the proximal portion. The distal portion of the C-shaped structure has a sharpened inner edge 8b facing in a proximal direction, which functions to cut through an item 10 when the item is held against the distal end 7a of the catheter 7 and a pulling force is applied to the pull wire 9. The device is intended to give a physician the ability to enter a cavity, such as a vein, and make contact with and hold or cut an item, such as an IVC filter or an IVC filter strut.

The cutting head 8 can be retracted into the catheter 7 of the removal assist device 6 for deployment or removal. This prevents the cutting head 8 from snagging on things as it is deployed, removed or repositioned during a procedure. The device 6, with the cutting head 8 in its retracted position within the catheter 7, can easily be pushed past an item, such as an IVC filter. The cutting head 8 can then be extended from the distal end 7a of the catheter 7. The physician can pull the cutting head 8 back while positioning it against the item to be removed until the cutting head 8 engages the item or portion of the item, such as an IVC filter strut 10. The cutting head 8 can then be partially retracted to grasp the item 10 as shown. Once the item 10 has been grasped, the physician can then use the catheter 7 to push/pull/rotate the item 10 and attempt to dislodge it.

If the physician is unable to dislodge the item 10, a cutter actuator 11 (FIG. 7) can be engaged to the proximal end of the catheter 7 and pull wire 9 of the removal assist device 6.

The actuator 11 can be used to increase the amount of force applied to the pull wire 9 to cause the cutting head 8 to cut the item 10, thereby freeing it. The cutting head 8 can then be retracted into the catheter 8 and repositioned to other items or portions of the same item that need assistance in freeing for removal.

The additional lumen of the filter retrieval device 5 of the present invention is oriented so any additional device or catheter, such as the removal assist catheter 6, which is inserted to assist in removal, is directed towards the vein wall, thereby preventing entrapment of the additional device in the filter itself.

A key feature of this filter retrieval device 5 is the fact that it can be rotated about its longitudinal axis allowing the removal assist catheter 6 to be swept along the vein wall to engage the legs, struts or embedded portion of the IVC filter.

Figure 5A:
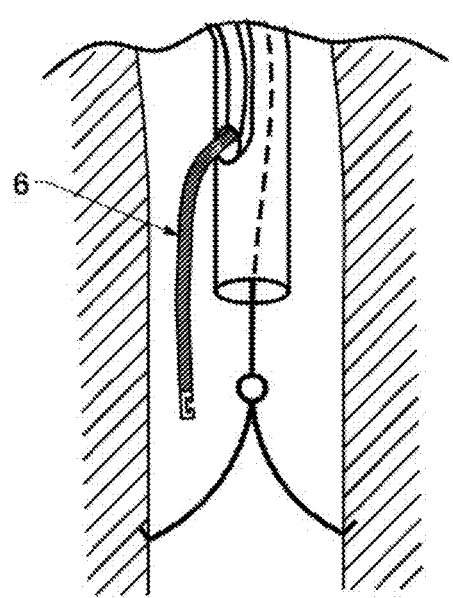
FIGS. 5A and 5B are a sequence of side elevation views showing a removal assist catheter being deployed out of the IVC filter retrieval device of the present invention.

The filter retrieval device 5 can be used by inserting the device 5 into the vasculature as is done with current sheaths (see FIG. 5A). A snare can be used to engage the IVC filter as is conventionally done. If the physician experiences difficulty in snaring the IVC filter, a balloon can be inserted in the additional lumen and inflated to stabilize the filter, and further attempts can be made to snare the filter. A diagnostic catheter can be inserted to infuse contrast media for external imaging. Additionally, an imaging catheter, such as an intravascular ultrasound catheter, can be used to assist in snaring the IVC filter. Once snared, if the IVC filter or portion of the IVC filter will not disengage from the vein wall, the physician can then use the additional lumen of the device 5 to insert a removal assist catheter, such as a cutter or a laser, to aid in removal of the filter.

Figure 5B:
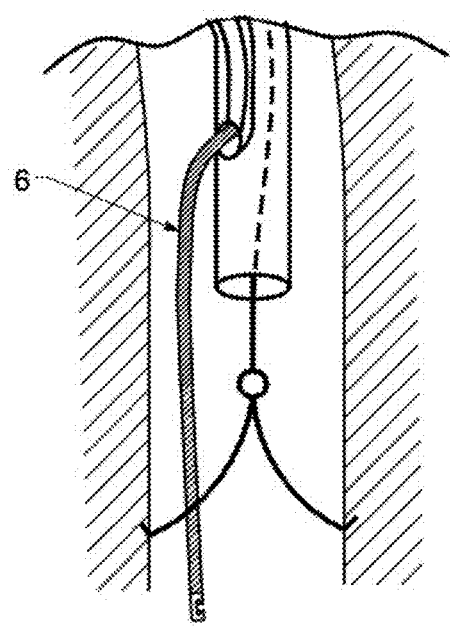

FIGS. 5A and 5B show the multi-lumen filter retrieval device 5 with the snare attached to the IVC filter. Also shown in FIGS. 5A and 5B is a removal assist catheter 6 extended though the multi-lumen sheath.

Figures 6A, 6B:
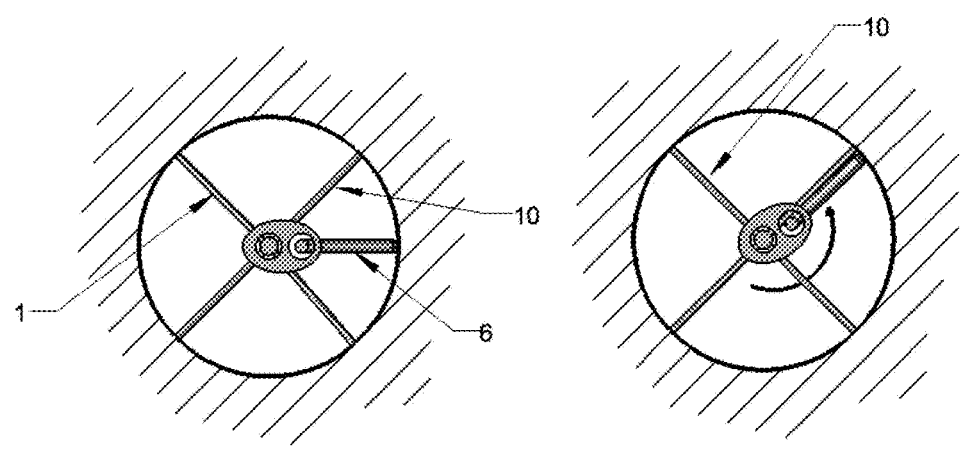
FIGS. 6A and 6B are a sequence of top views showing the filter retrieval device of the present invention being rotated to cause the removal assist catheter to engage an IVC filter strut.

The physician can advance the removal assist catheter 6 past the filter (FIG. 5B) and then rotate the device 5 until the removal assist catheter 6 makes contact with the filter strut 10 (see FIGS. 6A and 6B). The physician can then pull the removal assist catheter 6 back until it engages the filter. The physician can then use the removal assist catheter 6 to try and dislodge the filter from the vein wall or sever the filter at the vein wall.

The removal assist catheter 6 can then be rotated/retracted/extended until it makes contact with another embedded portion of the filter where the next section could be dislodged or severed. This process can be repeated until the filter is completely dislodged from the vein wall, which can be verified by rotating the multi-lumen device 5 360 degrees, ensuring there are no remaining portions of the filter lodged in the vein wall. This ability to rotate the device will also aid in positioning a balloon or imaging device during the procedure.

Figure 8:
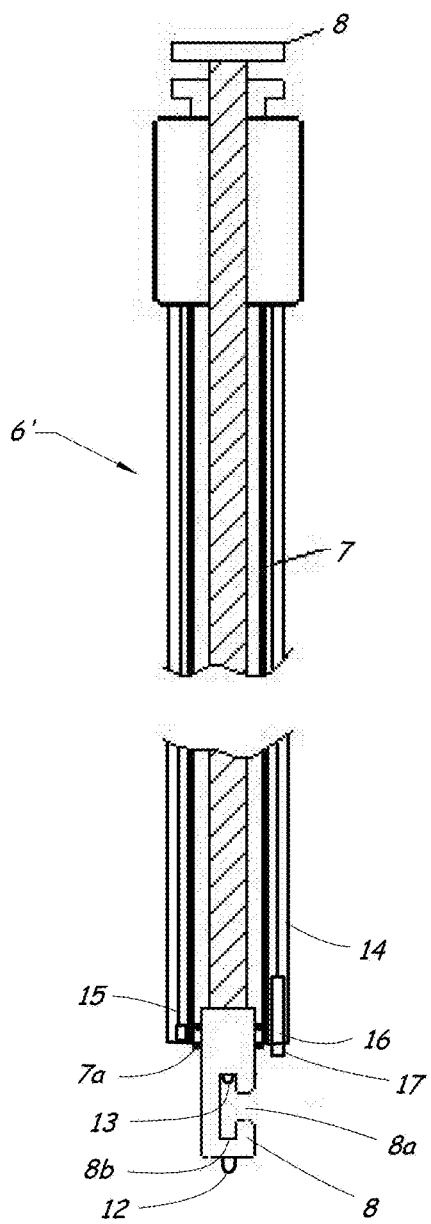
FIG. 8 is an elevation view of a modified device according to the present invention.
Figure 9:
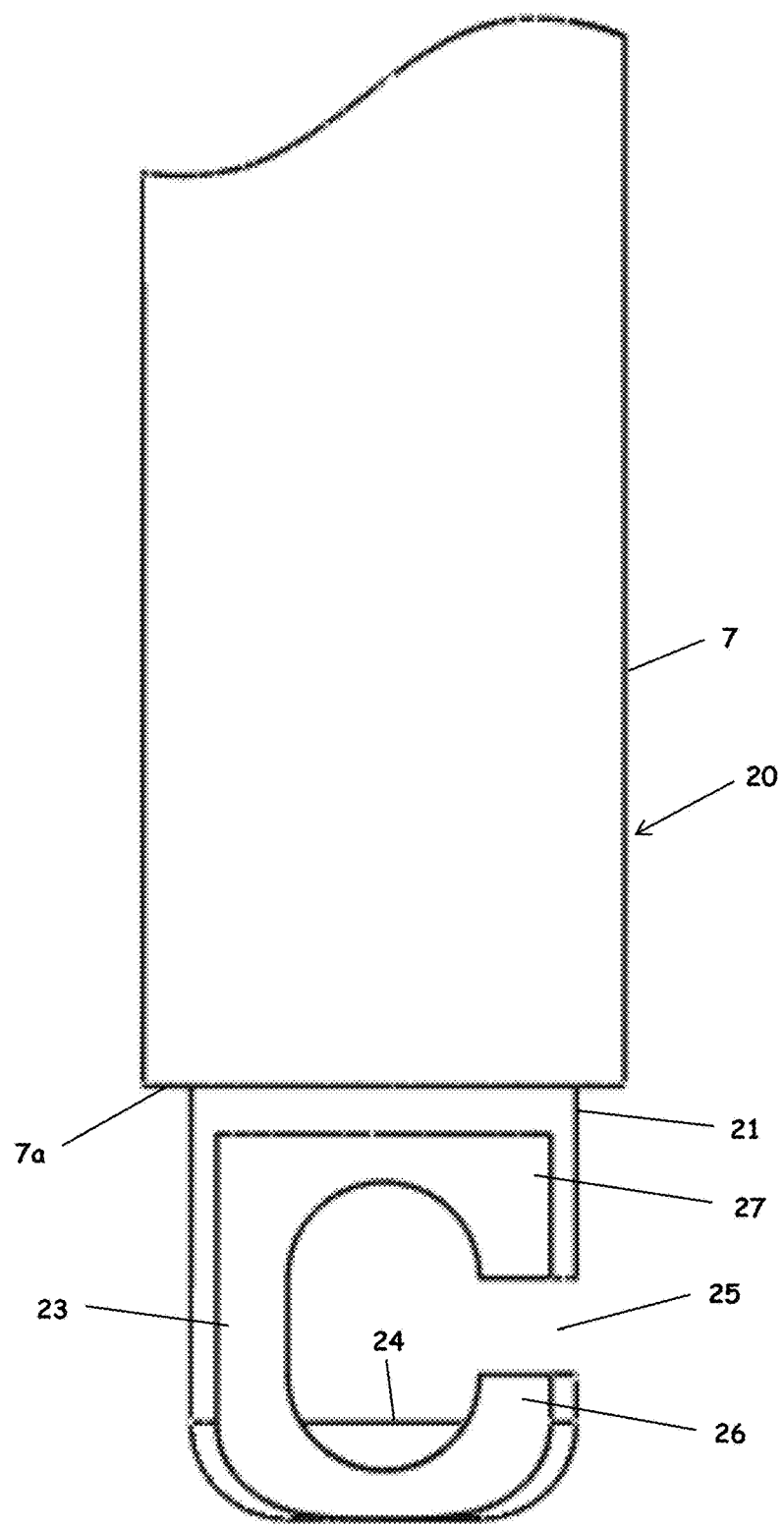
FIGS. 9 to 12 are various views of a removal assist device with a telescoping C-shaped cutting head.
Figure 10:
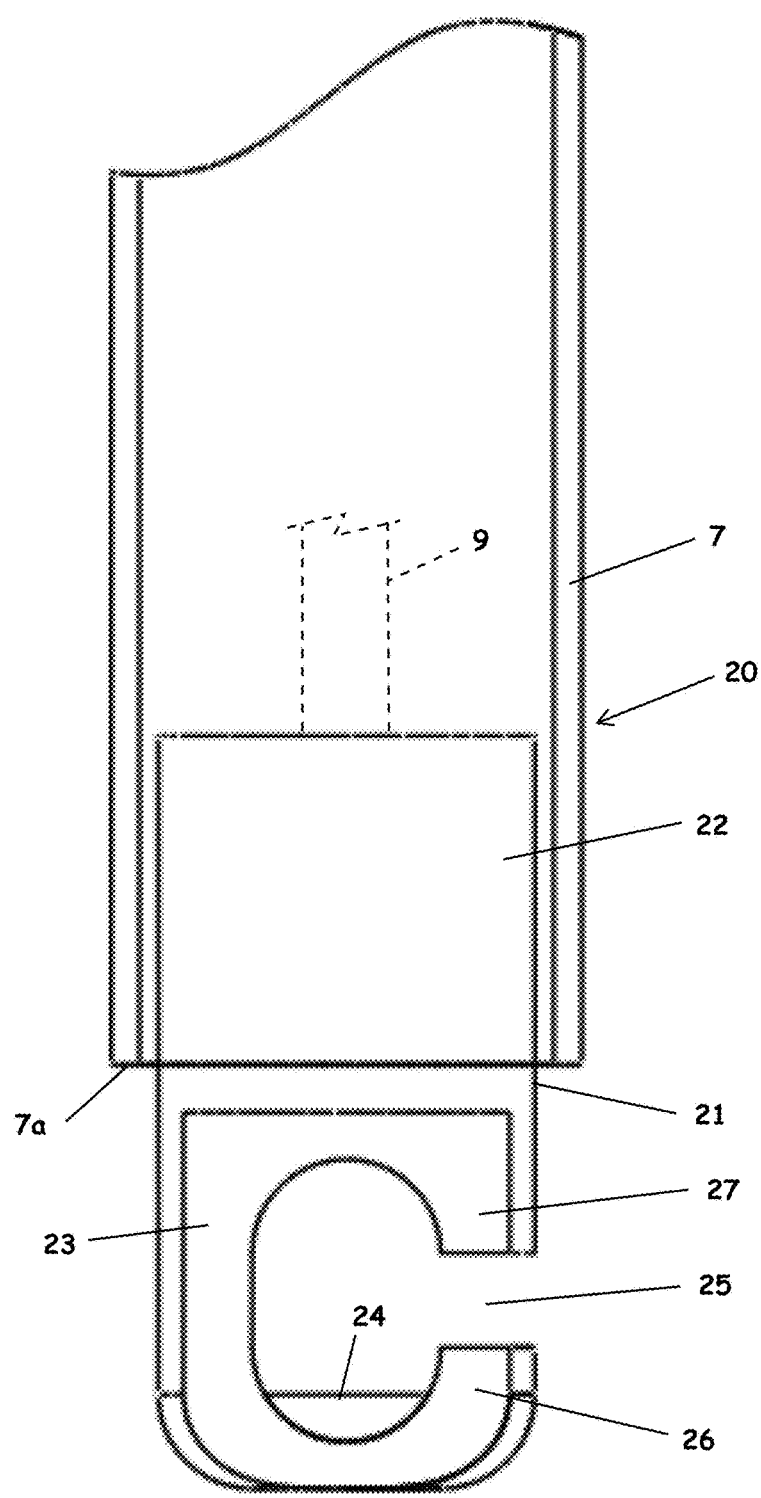
Figure 11:
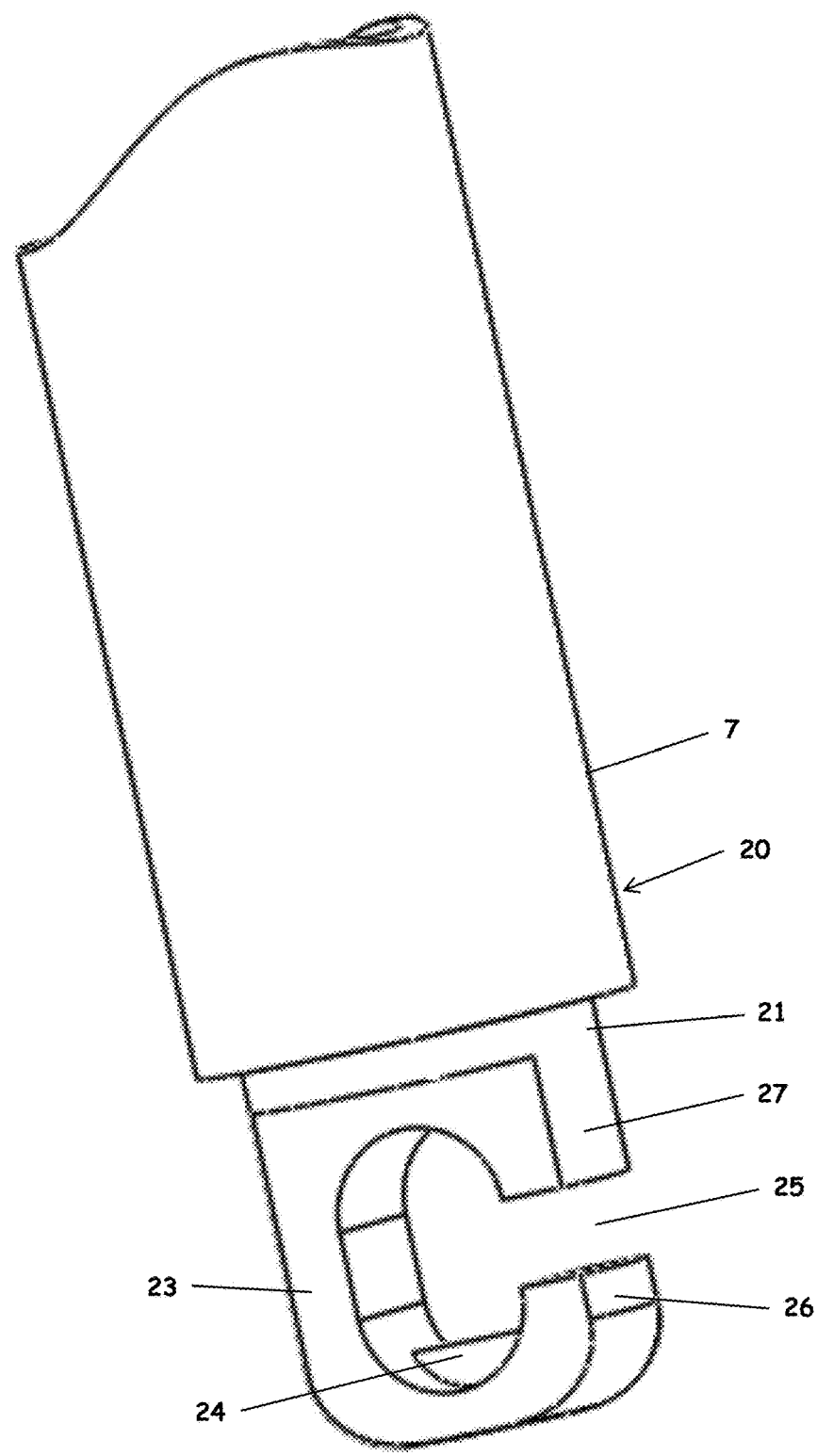
Figure 12:
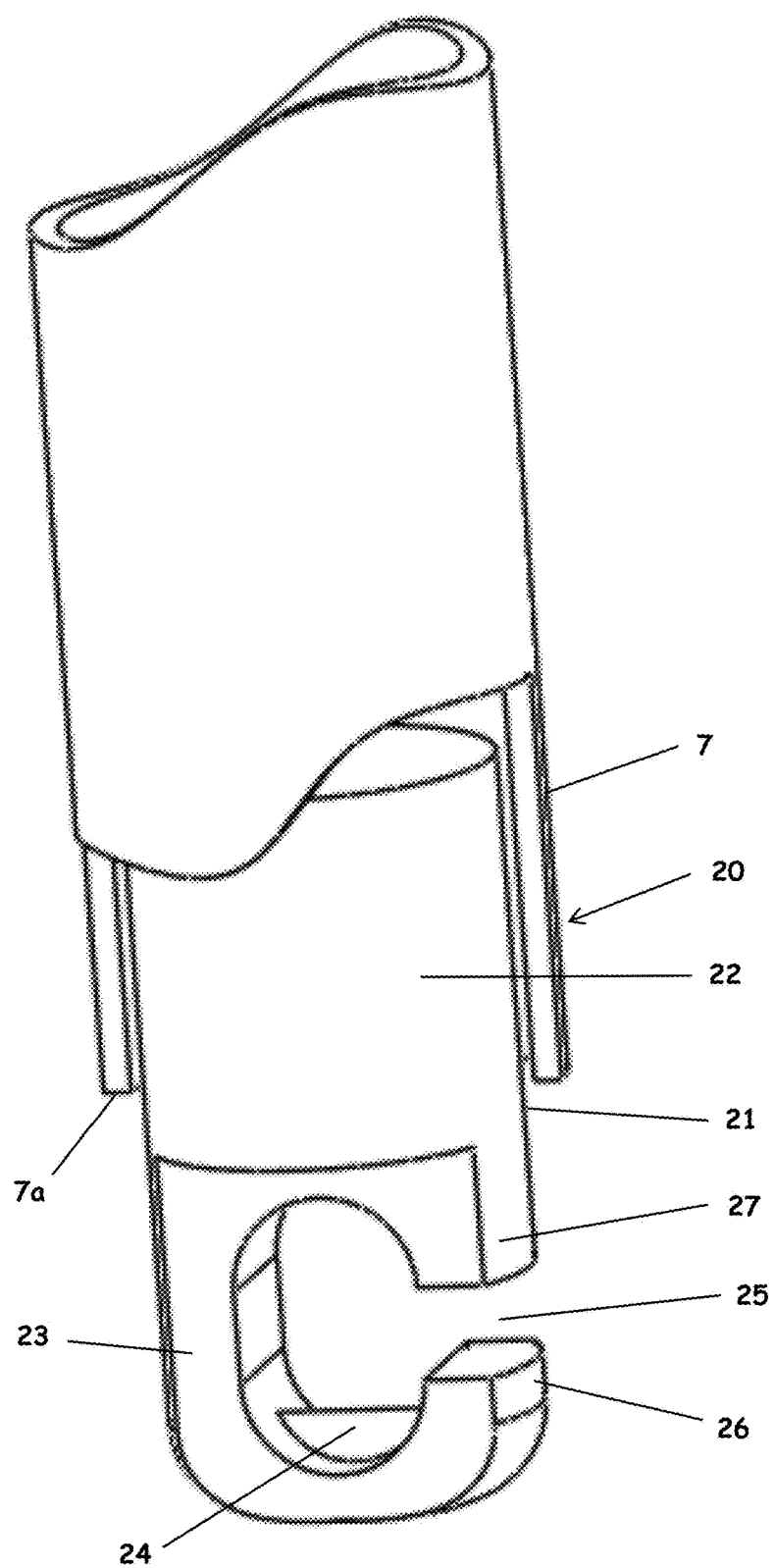
Figure 13:
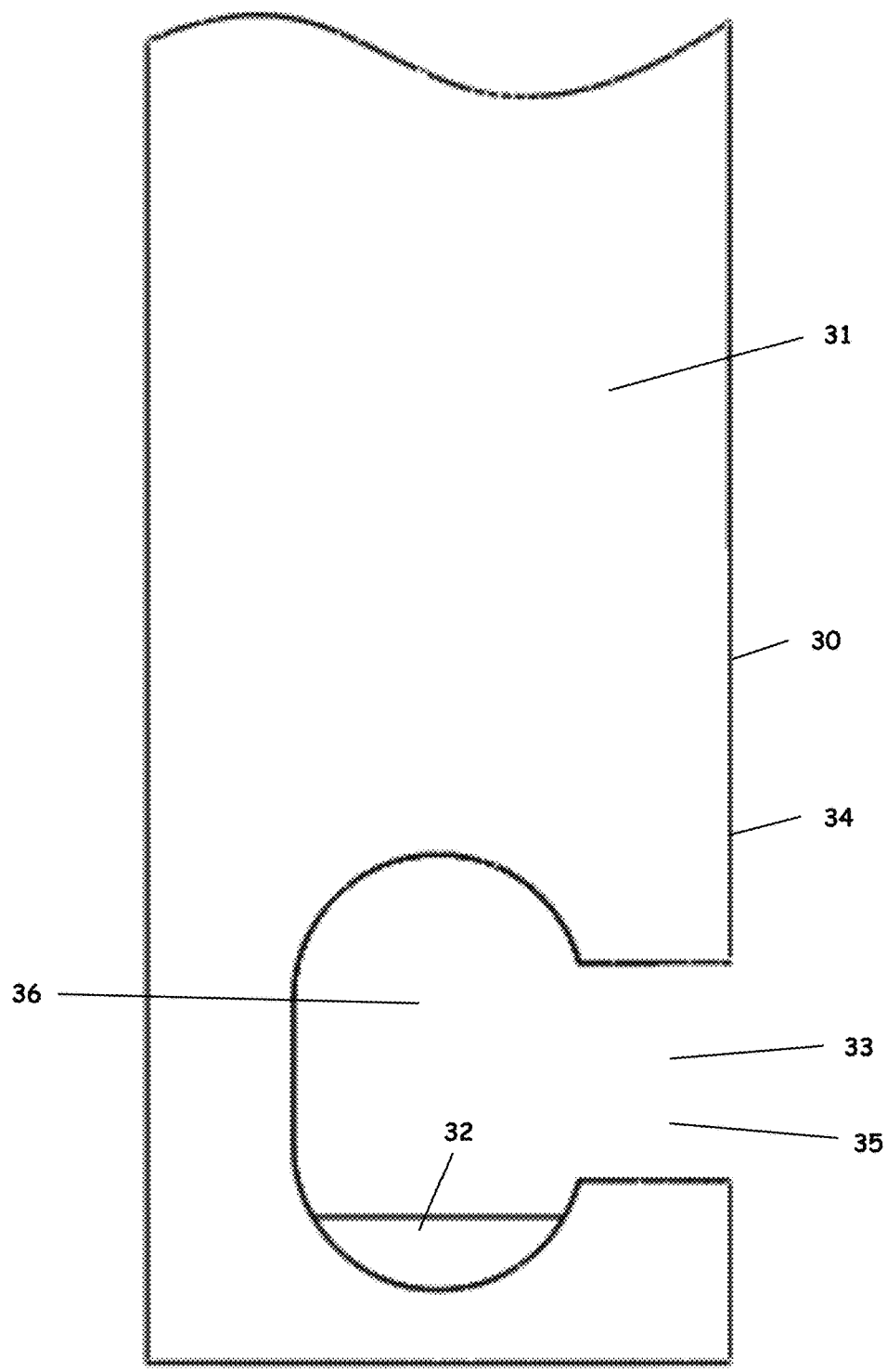
FIGS. 13 to 16 are various views of a tubular cutting head for use with the removal assist catheter of the present invention.
Figure 14:
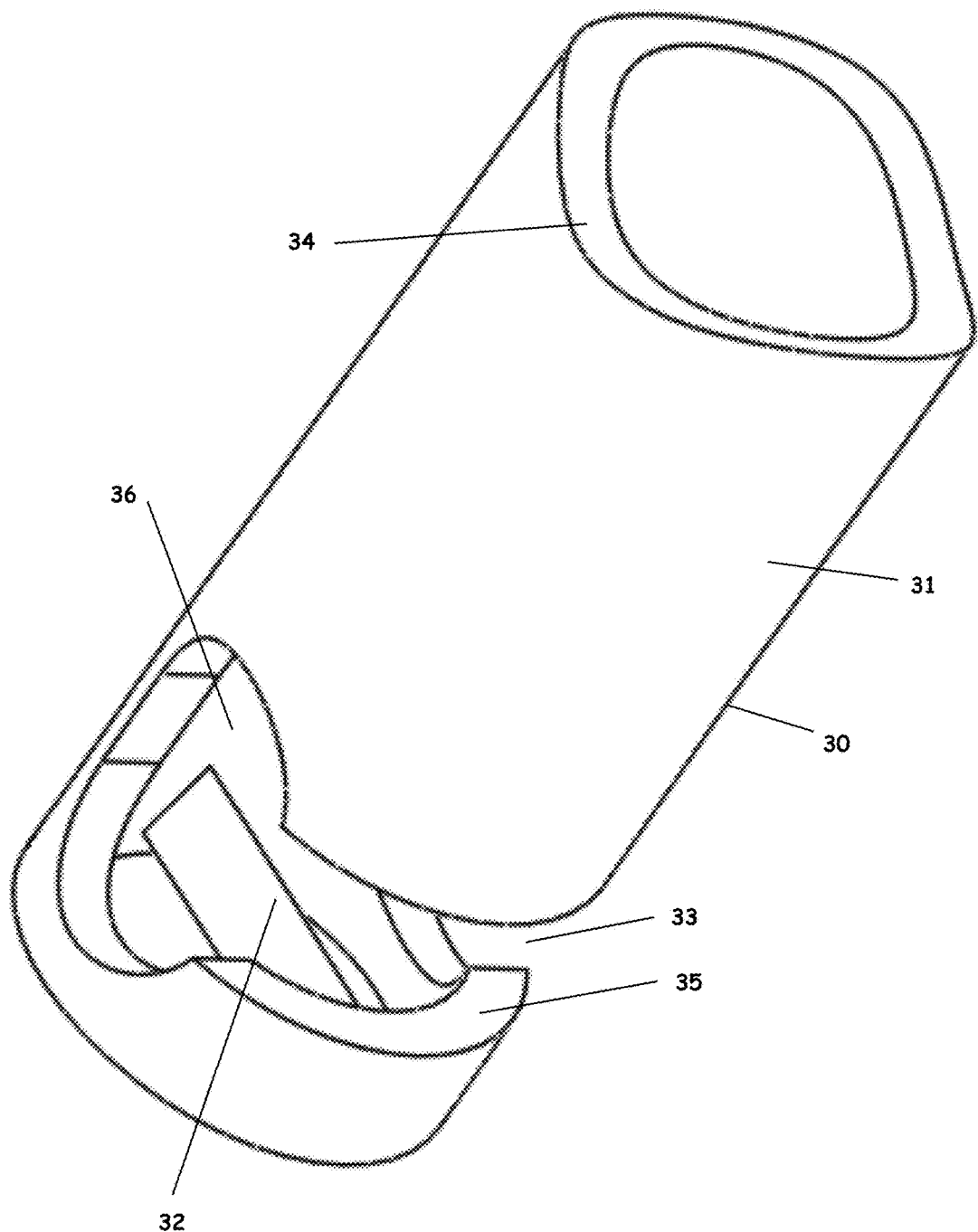
Figure 15:
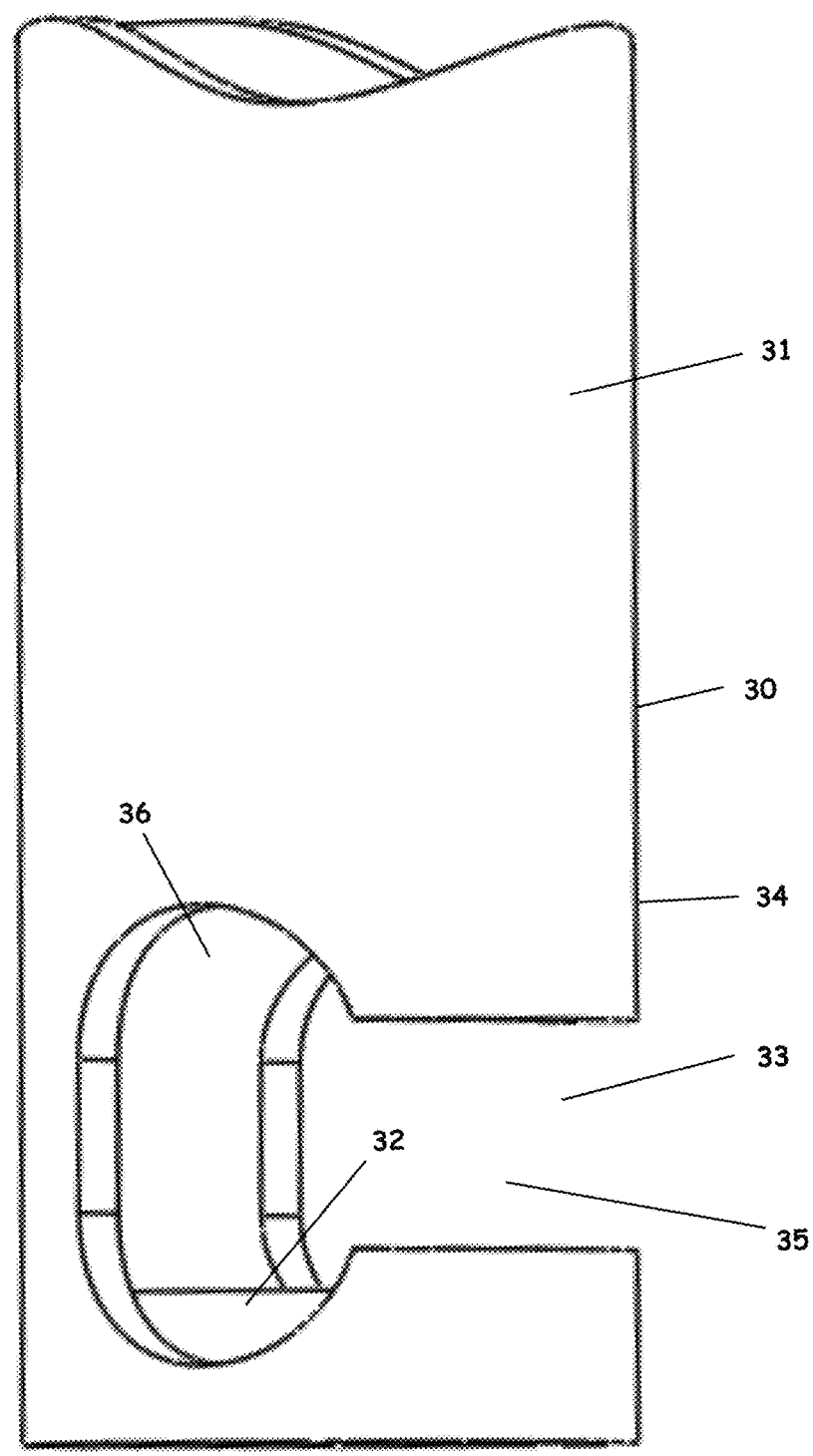
Figure 16:
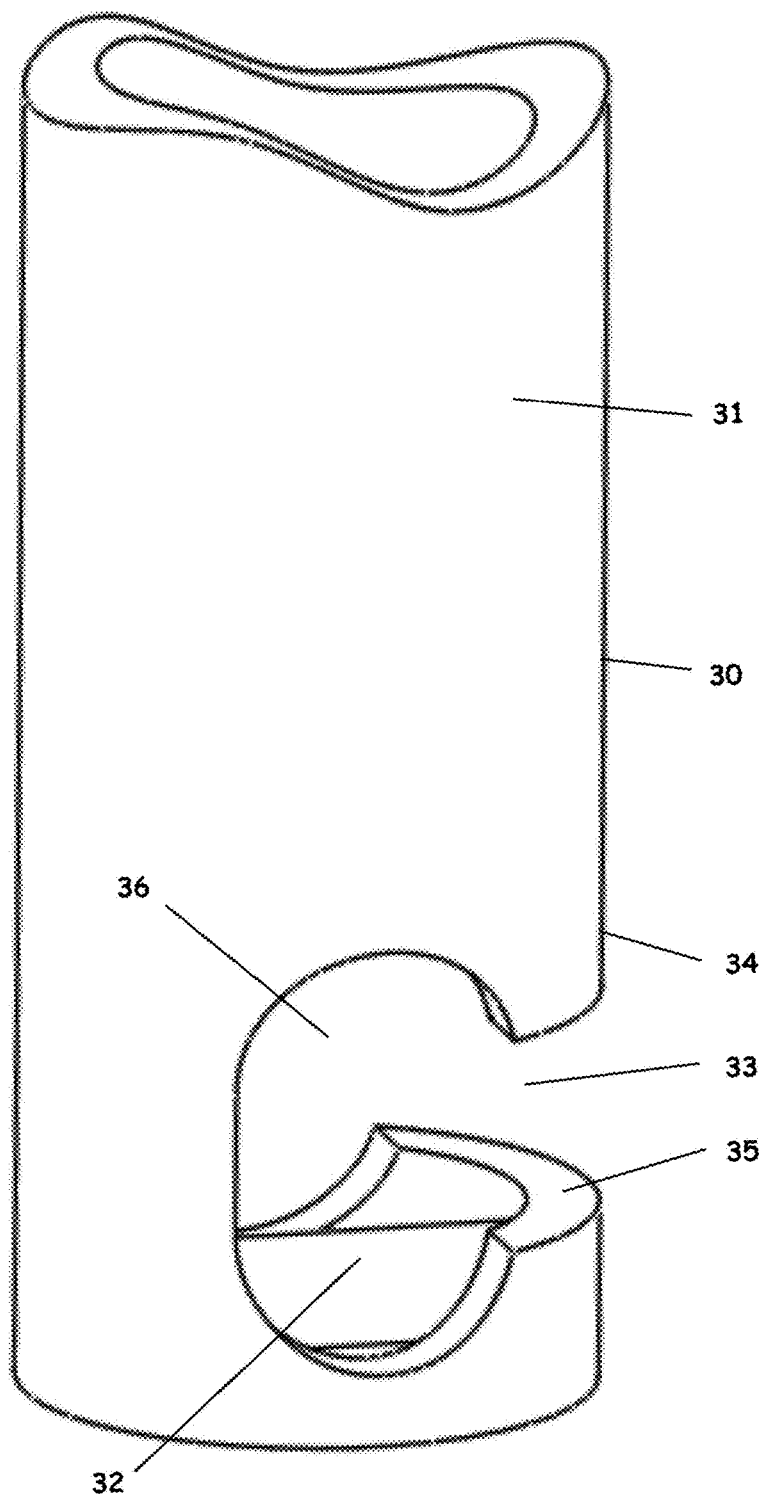

Additional features can be added to the removal assist device 6 to expand its capabilities and better adapt the device for performing certain procedures. FIG. 8 illustrates a modified device 6' that includes an imaging system 12, a laser cutter 13, an additional lumen 14, and a second pull wire 15. The imaging system 12 can be, for example, an intravascular ultrasound probe incorporated into the cutting head 8 for imaging the vessels in which the device 6' is used. The laser cutter 13 can be incorporated into the cutting head 8 or the catheter 7 to further assist in cutting procedures. The additional lumen 14 can be added for inserting a balloon 16 or imaging catheter 17 or a diagnostic catheter 14 for infusing contrast media without interfering with the operation of the cutting head 8. The second pull wire 15 can be added to the catheter 7 for deflecting the catheter 7 during deployment to aid in attaching the cutting head 8 to the IVC filter strut 10.

The multi lumen IVC filter retrieval device 5 has a first lumen that traverses an entire length of the sheath, and a second lumen that only traverses part of the length of the sheath and exits a side port through a sidewall of the sheath proximal of the distal end of the sheath. The second lumen is the same diameter through its entire length. The first lumen has a proximal portion occupied by the second lumen, and a distal portion which is distal of the side port and not occupied by the second lumen. The second lumen does not extend distal of the proximal portion of the first lumen. Therefore, the first lumen regains all of its inner diameter distal of the side port, allowing a larger space for retrieval of the IVC filter.

The multi lumen IVC filter retrieval device 5 can have a constant outer diameter that is the same outer diameter as current IVC retrieval catheters. Since the second lumen only extends to the side port, the distal portion of the first lumen has more space to contain the retrieved IVC filter and IVC retrieval snare, which are only pulled into the distal portion of the catheter.

The second lumen contains an assist device, such as the removal assist device 6, imaging system 12, laser cutter 13, balloon 16, and/or diagnostic catheter 14 for infusing contrast media. The distal portion of the first lumen provides a space unobstructed by the second lumen, thereby allowing a full inner diameter of the first lumen to contain a retrieved IVC filter and snare in the distal portion of the first lumen, while still providing access for the assist device in the second lumen.

Figure 7:
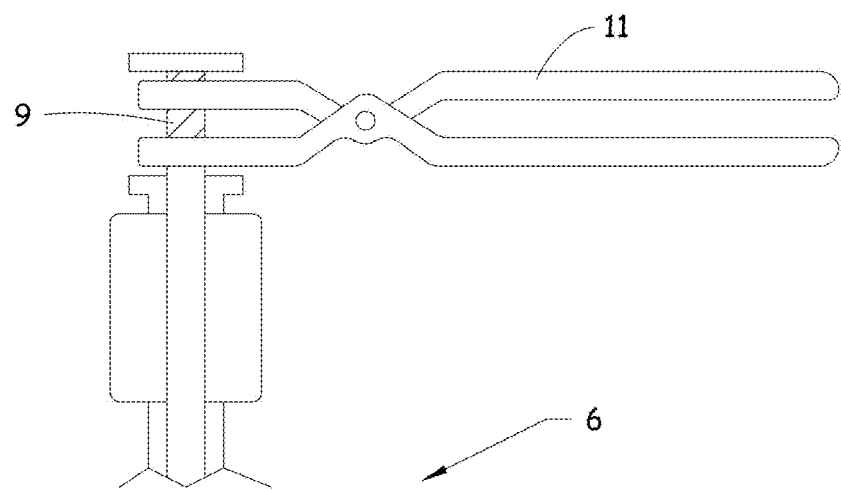
FIG. 7 is an elevation view of the removal assist device with the cutting head being used to grip and/or cut an IVC filter strut, and a cutter actuator at a proximal end for actuating the device.
Figure 7:
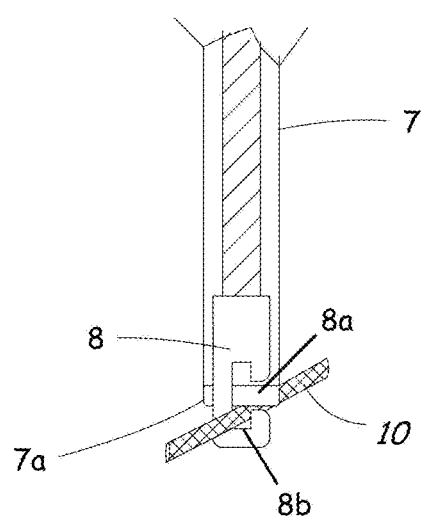

FIGS. 9 to 12 are various views of a removal assist device 20 with a telescoping C-shaped cutting head 21. The removal assist device 20 can be used in conjunction with the multi lumen IVC filter retrieval device 5 shown in FIGS. 3 to 6 and described above. The removal assist device 20 can also be used in conjunction with an actuator, as shown in FIG. 7, or additional features, as shown in FIG. 8. The cutting head 21 of the removal assist device 20 can be substituted for the cutting head 8 described above and shown in FIG. 7, and the same reference numerals will be used herein to refer to common features of these embodiments.

The removal assist device 20 includes a catheter 7 having a proximal end, a distal end 7a, and a lumen. The cutting head 21 is arranged within the lumen. A pull wire 9 has a proximal portion protruding from the proximal end of the catheter 7 and a distal end connected to the cutting head 21. The pull wire 9 is movable within the catheter to selectively extend and retract the cutting head 21 from the distal end of the catheter 7 to hold and/or cut an item to be retrieved.

The cutting head 21 includes a cylindrical guide portion 22 and a generally C-shaped holding and cutting portion 23. The C-shaped holding and cutting portion 23 is distal of the cylindrical guide portion 22. The cylindrical guide portion 22 is arranged to move in a telescoping manner within the lumen of the catheter 7. The cylindrical guide portion 22 closely mates to the interior surface of the tube/catheter 7 containing the cutting head 21. This keeps the cutting head 21 oriented properly and allows for cutting force to be applied while aligning the cutter blade 24 perpendicular to the item being cut.

The C-shaped holding and cutting portion 23 has an open lateral side 25 for receiving a portion of an item to be held or cut. The C-shaped holding and cutting portion 23 has a distal portion 26 and a proximal portion 27 with the open lateral side 25 located between the distal and proximal portions 26, 27. The distal portion 26 of the C-shaped holding and cutting portion 23 is arranged with a sharpened edge of the cutter blade 24 facing in a proximal direction to cut through an item when the item is held within the C-shaped structure against the distal end 7a of the catheter 7 and a pulling force is applied to the pull wire 9.

FIGS. 13 to 16 are various views of a tubular cutting head 30 for use with the removal assist catheter of the present invention. The tubular cutting head 30 can be used in conjunction with the removal assist device 6 shown in FIGS. 3 to 6 and 7, the removal assist device 6' shown in FIG. 8, or the removal assist device 20 shown in FIGS. 9 to 12. The tubular cutting head 30 can be substituted for the cutting head 8 shown in FIG. 7, or the cutting head 21 shown in FIGS. 9 to 12, and the same reference numerals will be used herein to refer to common features of these embodiments.

The tubular cutting head 30 is a tubular member with a cylindrical guide portion 31 arranged to move in a telescoping manner within the lumen of the catheter 7. The outer surface of the cylindrical guide portion 31 closely mates to the interior surface of the tube/catheter 7 containing the cutting head 30. This keeps the cutting head 30 oriented properly and allows for cutting force to be applied while aligning the cutting blade 32 perpendicular to the item being cut.

A cutout 33 is formed through a sidewall 34 of the tubular member 30 distal of the cylindrical guide portion 31. The cutout 33 has an open slot 35 on a lateral side of the tubular member 30 for receiving a portion of an item to be held or cut. A central opening 36 is connected to the open slot 35 and extends through opposite sides of the tubular member 30.

The cutting blade 32 has a sharpened edge facing in a proximal direction to cut through an item when the item is positioned within the central opening 36 of the tubular member 30. The tubular cutting head 30 is used in the same manner described above for the cutting head 8 shown in FIG. 7.

The open slot 35 and the central opening 36 of the cutout 33 define a C-shaped cutout in the sidewall 34 of the tubular member 30 when viewed in side view. The cutting blade 32 extends across an inner diameter of the tubular member 30 perpendicular to an axis of the central opening 36 through the tubular member 30. The cutting blade 32 can be attached to the inner portion of the tube and made to extend across the C-shaped cutout 33.

Alternatively, a cutting blade can be formed integral with one of the sidewalls 34 of the tubular member, with the other sidewall having a larger cutout area so that cutting action will only take place on the sidewall with the integral cutting blade. The shearing action between such a sidewall cutting blade and the end of the sheath in this arrangement will facilitate cutting.

While the invention has been specifically described in connection with a specific embodiment thereof, it is to be understood that this is by way of illustration and not of limitation, and the scope of the appended claims should be construed as broadly as the prior art will permit.

What is claimed is:

1. A multi lumen IVC filter retrieval device, comprising:
a sheath having a first lumen that traverses an entire length of the sheath, said first lumen having a proximal portion and a distal portion, said first lumen containing a snare that can be deployed out a distal end of the sheath and retracted back into the distal portion of the first lumen;
said sheath having a second lumen within the proximal portion of said first lumen, said second lumen opens through a sidewall of the sheath proximal of the distal end of the sheath so that said second lumen does not extend distal of said proximal portion of said first lumen into said distal portion thereof, wherein said second lumen occupies the proximal portion of said first lumen but does not occupy the distal portion of said first lumen;

said second lumen contains an assist device that can be deployed through the sidewall of the sheath and used during an IVC filter retrieval procedure; and said distal portion of the first lumen provides a space unobstructed by said second lumen, thereby allowing a full inner diameter of said first lumen to contain a retrieved IVC filter and snare in the distal portion of the first lumen while still providing access for the assist device in the second lumen.

2. The device according to claim 1, wherein said assist device comprises a removal assist device that can be deployed through the sidewall of the sheath and used to assist removal of an IVC filter to be retrieved from a vein wall.

3. The device according to claim 2, wherein said removal assist device is a removal assist catheter having a pull wire and a cutting head attached to the pull wire that can be extended out a distal end of the catheter and used to hold and/or cut the IVC filter to be retrieved.

4. The device according to claim 3, wherein said sheath is rotatable about its longitudinal axis to allow the removal assist catheter to be swept along a vein wall to engage the IVC filter to be retrieved.

5. The device according to claim 3, wherein said cutting head comprises a generally C-shaped structure having an open lateral side for receiving a portion of the IVC filter to be retrieved.

6. The device according to claim 5, wherein said C-shaped structure has a distal portion and a proximal portion with said open lateral side positioned between said distal portion and said proximal portion, and said distal portion of said C-shaped structure has a sharpened inner edge facing in a proximal direction which is arranged to cut through a portion of the IVC filter when the portion of the IVC filter is held within the C-shaped structure against the distal end of the catheter and a pulling force is applied to the pull wire.

7. The device according to claim 1, wherein said assist device comprises a balloon.

8. The device according to claim 1, wherein said assist device comprises an imaging device.

9. The device according to claim 1, wherein said assist device comprises a diagnostic catheter for infusing contrast media.

10. The device according to claim 1, wherein said assist device comprises a laser cutter to assist in cutting procedures.

11. The device according to claim 1, wherein said assist device comprises:

a catheter having a proximal end, a distal end, and a lumen;

a cutting head arranged within said lumen of the catheter; and a pull wire having a proximal portion protruding from the proximal end of the catheter and a distal end connected to the cutting head, said pull wire being movable within the catheter to selectively extend and retract the cutting head from the distal end of the catheter to hold and/or cut an item to be retrieved;

said cutting head comprising a cylindrical guide portion and a generally C-shaped holding and cutting portion, said C-shaped holding and cutting portion being distal of said cylindrical guide portion, and said cylindrical guide portion being arranged to move in a telescoping manner within said lumen of the catheter, and said C-shaped holding and cutting portion having an open lateral side for receiving a portion of an item to be held or cut.

12. The device according to claim 11, wherein said C-shaped holding and cutting portion has a distal portion and a proximal portion with said open lateral side located between said distal portion and said proximal portion, and said distal portion of said C-shaped holding and cutting portion has a sharpened edge facing in a proximal direction which is arranged to cut through an item when the item is held within the C-shaped structure against the distal end of the catheter and a pulling force is applied to the pull wire.

13. The device according to claim 11, wherein said cylindrical guide portion and said C-shaped holding and cutting portion are integral with each other and formed from a tubular member.

14. The device according to claim 13, wherein said tubular member has a sidewall and a C-shaped cutout through said sidewall that defines an opening for said C-shaped holding and cutting portion.

15. The device according to claim 14, further comprising a cutting blade with a sharpened edge facing in a proximal direction which is arranged to cut through an item when the item is positioned within the C-shaped cutout of the tubular member.

16. The device according to claim 1, wherein said assist device comprises:

a catheter having a proximal end, a distal end, and a lumen;

a cutting head arranged within said lumen of the catheter; and a pull wire having a proximal portion protruding from the proximal end of the catheter and a distal end connected to the cutting head, said pull wire being movable within the catheter to selectively extend and retract the cutting head from the distal end of the catheter to hold and/or cut an item to be retrieved;

said cutting head comprising a tubular member having a cylindrical guide portion arranged to move in a telescoping manner within said lumen of the catheter, and a cutout through a sidewall of said tubular member distal of said cylindrical guide portion, said cutout having an open slot on a lateral side of said tubular member for receiving a portion of an item to be held or cut, and a central opening connected to said open slot extending through opposite sides of said tubular member, and a cutting blade with a sharpened edge facing in a proximal direction arranged to cut through an item when the item is positioned within the central opening of the tubular member.

17. The device according to claim 16, wherein said open slot and said central opening of said cutout define a C-shaped cutout in the sidewall of the tubular member when viewed in side view.

18. The device according to claim 16, wherein said cutting blade extends across an inner diameter of said tubular member perpendicular to an axis of the central opening through the tubular member.

\* \* \* \* \*